United States Patent
Pauley et al.

(10) Patent No.: US 12,029,844 B2
(45) Date of Patent: Jul. 9, 2024

(54) COMBINATION SPIROMETER-INHALER

(71) Applicant: Willow Laboratories, Inc., Irvine, CA (US)

(72) Inventors: Kevin Hughes Pauley, Lake Forest, CA (US); Sai Kong Frank Lee, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 519 days.

(21) Appl. No.: 17/355,752

(22) Filed: Jun. 23, 2021

(65) Prior Publication Data

US 2021/0402110 A1     Dec. 30, 2021

Related U.S. Application Data

(60) Provisional application No. 63/071,310, filed on Aug. 27, 2020, provisional application No. 63/044,269, filed on Jun. 25, 2020.

(51) Int. Cl.
    *A61M 15/00*     (2006.01)
(52) U.S. Cl.
    CPC ...... *A61M 15/002* (2014.02); *A61M 15/0018* (2014.02); *A61M 15/0021* (2014.02);
    (Continued)
(58) Field of Classification Search
    CPC ............ A61M 15/002; A61M 15/0018; A61M 15/0021; A61M 2205/3334; A61M 2205/3576; A61M 2205/583; A61M 2230/205; A61M 2230/42; A61M 15/0013; A61M 2016/0039; A61M 2016/0042; A61M 2205/332; A61M 2205/3375; A61M 2205/3553; A61M 2205/3592; A61M 2205/505; A61M 2205/52;
    (Continued)

(56) References Cited

U.S. PATENT DOCUMENTS

| 492,973 A | * | 3/1893 | Shepard | ................. | A61B 5/095 |
|---|---|---|---|---|---|
| | | | | | 128/200.11 |
| 895,606 A | * | 8/1908 | Warde | ..................... | A61B 5/09 |
| | | | | | 600/539 |

(Continued)

FOREIGN PATENT DOCUMENTS

| WO | WO 2017/141033 | 8/2017 | | |
| WO | WO-2021194880 A1 | * | 9/2021 | ........... A61B 5/0205 |
| WO | WO 2021/262877 | 12/2021 | | |

OTHER PUBLICATIONS

International Search Report and Written Opinion received in PCT Application No. PCT/US2021/038733 dated Oct. 20, 2021.

*Primary Examiner* — Victoria Murphy
(74) *Attorney, Agent, or Firm* — Knobbe, Martens, Olson & Bear, LLP

(57) ABSTRACT

Various spirometer-inhaler systems and devices are disclosed. The spirometer-inhaler system may estimate physiological parameters of a user based on the user's inhaled and/or exhaled breaths received by the spirometer-inhaler device. The spirometer-inhaler device may comprise one or more flow paths. A first flow path may direct medication from a medicine canister to an opening of the device. A second flow path may direct a user's exhaled breath from the opening of the device to one or more flow measurement devices.

18 Claims, 5 Drawing Sheets

(52) U.S. Cl.
CPC ............... *A61M 2205/3334* (2013.01); *A61M 2205/3576* (2013.01); *A61M 2205/583* (2013.01); *A61M 2230/205* (2013.01); *A61M 2230/42* (2013.01)

(58) Field of Classification Search
CPC ...... A61M 2205/8206; A61M 2206/20; A61M 2230/04; A61M 2230/06; A61M 2230/20; A61M 2230/30; A61M 2230/40; A61M 2230/50; A61M 2230/62; A61M 2230/63; A61M 15/009; A61B 5/02055; A61B 5/021; A61B 5/024; A61B 5/14532; A61B 5/14551; A61B 5/087; A61B 5/4839; G16H 10/60; G16H 20/13; G16H 40/63; G16H 40/67
See application file for complete search history.

(56) References Cited

U.S. PATENT DOCUMENTS

| | | | |
|---|---|---|---|
| 4,148,308 A * | 4/1979 | Sayer | A61B 1/24 128/207.14 |
| 4,960,128 A | 10/1990 | Gordon et al. | |
| 4,964,408 A | 10/1990 | Hink et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,724,986 A | 3/1998 | Jones et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,890,929 A | 4/1999 | Mills et al. | |
| 5,919,134 A | 7/1999 | Diab | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,358,058 B1 * | 3/2002 | Strupat | A61M 15/0065 434/262 |
| 6,360,114 B1 | 3/2002 | Diab et al. | |
| 6,368,283 B1 | 4/2002 | Xu et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,658,276 B2 | 12/2003 | Kiani et al. | |
| 6,661,161 B1 | 12/2003 | Lanzo et al. | |
| 6,697,656 B1 | 2/2004 | Al-Ali | |
| 6,697,658 B2 | 2/2004 | Al-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,920,345 B2 | 7/2005 | Al-Ali et al. | |
| 6,934,570 B2 | 8/2005 | Kiani et al. | |
| 6,943,348 B1 | 9/2005 | Coffin, IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |

(56) References Cited

U.S. PATENT DOCUMENTS

| | | |
|---|---|---|
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |

(56) References Cited

U.S. PATENT DOCUMENTS

| | | |
|---|---|---|
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0239058 A1 | 10/2007 | Krasilchikov et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2010/0004518 A1 | 1/2010 | Vo et al. |
| 2010/0030040 A1 | 2/2010 | Poeze et al. |

(56) References Cited

U.S. PATENT DOCUMENTS

| | | |
|---|---|---|
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0120455 A1 | 5/2011 | Murphy |
| 2011/0137297 A1 | 6/2011 | Kiani et al. |
| 2011/0172498 A1 | 7/2011 | Olsen et al. |
| 2011/0180067 A1* | 7/2011 | Avni ............... A61M 15/00 128/204.23 |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0273165 A1* | 10/2015 | Hadash ............... A61M 16/202 128/203.14 |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0310823 A1 | 11/2018 | Al-Ali et al. |
| 2019/0046079 A1* | 2/2019 | Reed ............... A61M 15/0021 |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0268990 A1* | 8/2020 | Ash ............... A61M 15/00 |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0146147 A1* | 5/2021 | Alizoti ............... A61M 15/009 |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |

\* cited by examiner

COMBINATION SPIROMETER-INHALER

INCORPORATION BY REFERENCE TO ANY PRIORITY APPLICATIONS

This application claims the benefit of priority to U.S. Provisional App. No. 63/044,269 entitled "COMBINATION SPIROMETER-INHALER," filed Jun. 25, 2020 and U.S. Provisional App. No. 63/071,310 entitled "COMBINATION SPIROMETER-INHALER," filed Aug. 27, 2020. Each of these applications are hereby incorporated by reference herein in their entireties. Any and all applications for which a foreign or domestic priority claim is identified in the Application Data Sheet as filed with the present application are hereby incorporated by reference and made a part of the present disclosure.

FIELD OF THE DISCLOSURE

The general field of this disclosure is systems and devices related to managing a user's respiratory condition.

BACKGROUND

Spirometers are often used to diagnose a variety of chronic lung conditions, such as asthma and chronic obstructive pulmonary disease ("COPD"), that may require the use of control and rescue inhalers. To complete a spirometer maneuver, many current spirometers require a user to attempt to use full tidal volume of their lungs and blow through a wide hole. Such a maneuver can result in coughing and general discomfort. Additionally, treatment of chronic lung conditions may require users carry around a number of items, including rescue medication, control medication, inhaler, spirometer, and a tracking device.

SUMMARY

In some aspects of the disclosure, a spirometer-inhaler device for managing a user's respiratory condition is disclosed. A spirometer-inhaler device can include: a first portion that can removably receive a medicine canister; a second portion that can extend from the first portion and include a mouthpiece; a first flow path that can direct medication from the medicine canister to the opening of the mouthpiece; and a second flow path that can direct exhaled air from the opening of the mouthpiece to one or more flow rate measurement devices. The mouthpiece can include an opening and one or more propellers. The second flow path can include one of the one or more propellers.

In some aspects, the first portion can include a central cavity that can removably receive the medicine canister.

In some aspects, the first portion can optionally include a one way valve that can removably connect to the medicine canister and direct medication from the medicine canister to the opening of the mouthpiece.

In some aspects, the first flow path can include the one way valve and the opening of the mouthpiece.

In some aspects, the one way valve can form a seal with the medicine canister.

In some aspects, the seal can prevent the exhaled air from entering the first flow path.

In some aspects, the one way valve can deliver the medication from the medicine canister to the opening of the mouthpiece via the first flow path.

In some aspects, the first portion may not include a valve. For example, the first portion may include an interior gap that can direct medication from the medicine canister to the opening of the mouthpiece.

In some aspects, the spirometer-inhaler device can further include an interior flow pathway with a first end and a second end.

In some aspects, the second flow path can include the interior flow pathway and the opening of the mouthpiece.

In some aspects, the first end of the interior flow pathway can be located adjacent the opening of the mouthpiece. The second end of the interior flow pathway can be located on a side portion of the first portion.

In some aspects, the second flow path can further include at least one cover.

In some aspects, the at least one cover can include at least one shutter. The at least one shutter can include a lever portion and a cover portion that can cover the second end of the interior flow pathway.

In some aspects, the cover portion of the at least one shutter can be removed from the second end of the interior flow pathway in response to a user actuating the lever portion of the at least one shutter.

In some aspects, the at least one cover can include one or more of: a manual plug, a rotatable cover, a mechanical iris, or a cuspid one-way valve.

In some aspects, the interior flow pathway can include an interior tube.

In some aspects, the interior flow pathway can include a plurality of interior ribs. The plurality of interior ribs can guide the second flow path from the opening of the mouthpiece to the second end of the plurality of interior ribs.

In some aspects, the second end of the interior flow pathway can removably connect to the one or more flow rate measurement devices.

In some aspects, the spirometer-inhaler device can further include a display.

In some aspects, the display can be disposed on the first portion.

In some aspects, the spirometer-inhaler can further include at least one processor that can estimate one or more physiological parameters of the user based on measurements from the device.

In some aspects, the spirometer-inhaler device can further include a transmitter.

In some aspects, the transmitter can transmit the one or more physiological parameters of the user to one or more of: a network, a backend system, or one or more user devices.

In some aspects, the first flow path can include a propeller of the one or more propellers.

In some aspects, the propeller can be positioned adjacent the opening of the mouthpiece.

In some aspects, the propeller can spin in response to a negative flow rate within the mouthpiece.

In some aspects, the at least one processor can begin taking measurements in response to the propeller spinning.

In some aspects, the negative flow rate can be created within the mouthpiece by the user inhaling from the opening of the mouthpiece in use.

In some aspects, a propeller of the one or more propellers can be operatively connected to a turbine.

In some aspects of the disclosure, a system for delivering a medication to a user and measuring a plurality of physiological parameters of the user is disclosed. The system can include: a spirometer-inhaler device; a medicine canister that can deliver the medication to a first portion of the spirometer-inhaler device; and one or more measurement devices that can estimate one or more physiological parameters of the user. The spirometer-device can include: the first portion that can removably receive the medicine canister; a second portion that can extend from the first portion and include a mouthpiece that can include an opening and one or more propellers; a first flow path that can direct the medication from the medicine canister to the opening of the mouthpiece; and a second flow path that can direct exhaled air from the opening of the mouthpiece to one or more flow rate measurement devices. The second flow path can include one of the one or more propellers. The one or more measurement devices can include the one or more flow rate measurement devices.

In some aspects, the spirometer-inhaler device can further include a central hole that can removably receive the medicine canister.

In some aspects, the spirometer-inhaler device can further include a one way valve that can removably connect to the medicine canister and direct medication from the medicine canister to the opening of the mouthpiece.

In some aspects, the medicine canister can deliver the medication to the one way valve.

In some aspects, the first flow path can include the one way valve and the opening of the mouthpiece.

In some aspects, the central hole of the first portion can include an internal gap. The internal gap can direct medication from the medicine canister to the opening of the mouthpiece.

In some aspects, the spirometer-inhaler device can further include an interior flow pathway with a first end and a second end.

In some aspects, the first end of the interior flow pathway can be located adjacent the opening of the second portion and the second end of the interior flow pathway can be located on a side portion of the first portion.

In some aspects, the second flow path can include the interior flow pathway and the opening of the mouthpiece.

In some aspects, the second end of the interior flow pathway can be connectable to the one or more flow rate measurement devices.

In some aspects, the interior flow pathway can include one or more of: one or more interior tubes or one or more interior ribs.

In some aspects, the one or more flow rate measurement devices can estimate at least one of: forced inspiratory flow, force expiratory volume, forced expiratory flow, force vital capacity, maximal voluntary ventilation, inspiratory reserve volume, expiratory reserve volume, residual volume, functional residual capacity, total lung capacity, inspiratory capacity, tidal volume, vital capacity, maximal inspiratory pressure, or maximal expiratory pressure.

In some aspects, the one or more flow rate measurement devices can be connectable to the second flow path.

In some aspects, the one or more measurement devices can measure at least one of: oxygen saturation, respiratory rate, total hemoglobin level, level of carboxyhemoglobin, level of methemoglobin, pulse rate, or acoustic measurements.

In some aspects, the system can further include a display.

In some aspects, the display can be disposed on one or more of: the spirometer-inhaler device, the one or more measurement devices, or one or more user devices.

In some aspects, the system can further include a transmitter.

In some aspects, the transmitter can transmit the one or more physiological parameters of the user to one or more of: a network, a backend system, or one or more user devices.

BRIEF DESCRIPTION OF THE DRAWINGS

The following drawings and the associated descriptions are provided to illustrate embodiments of the present disclosure and do not limit the scope of the claims.

DETAILED DESCRIPTION

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Figure 1:
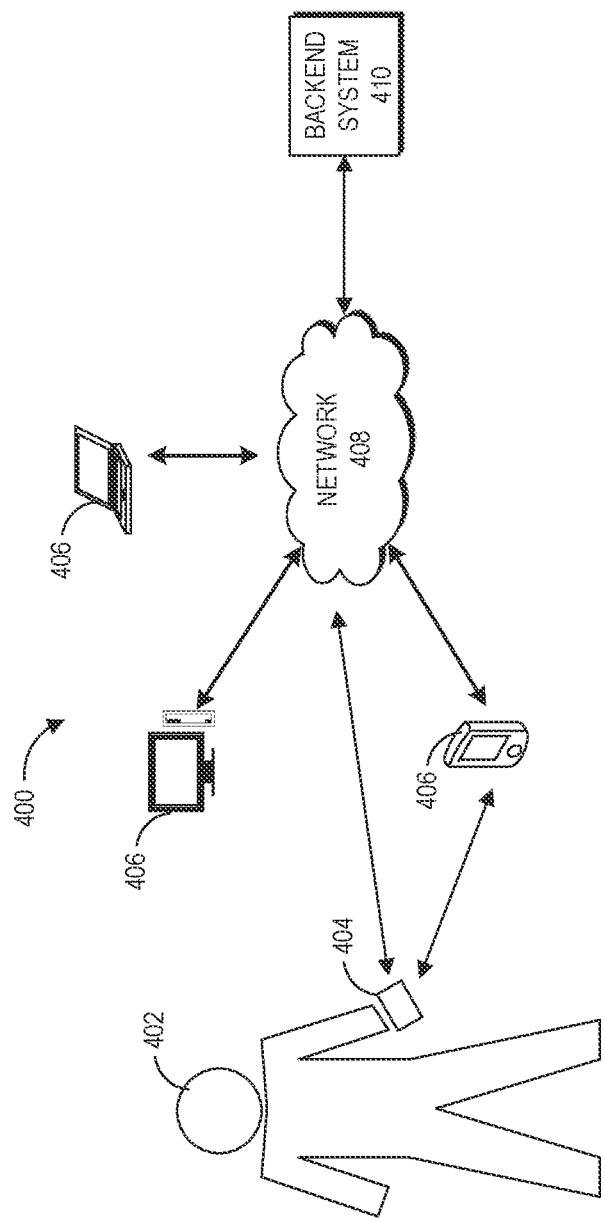
FIG. 1 illustrates a block diagram of an example use environment for a spirometer-inhaler device.
Figure 2:
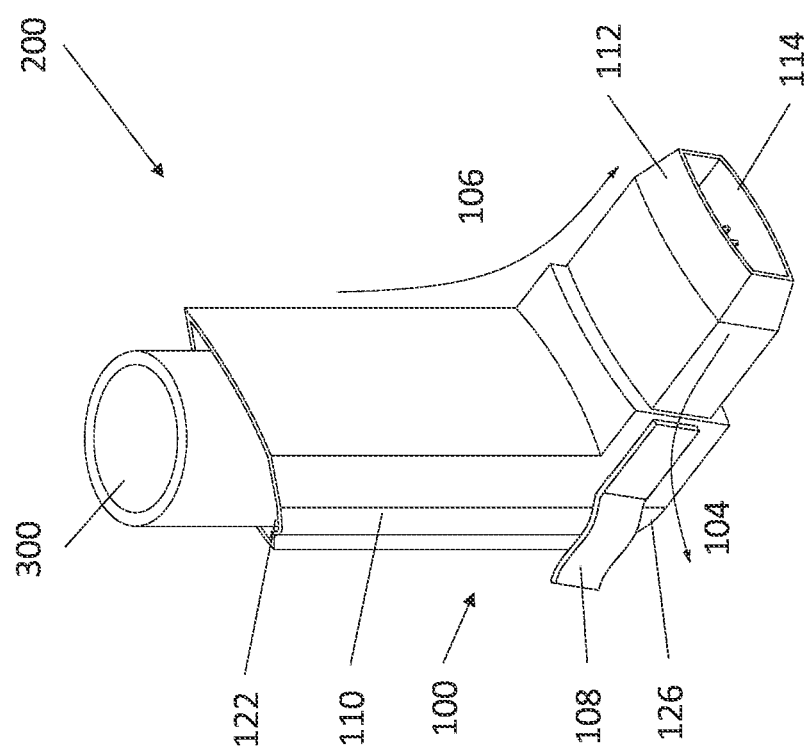
FIGS. 2-3 illustrate perspective views of a spirometer-inhaler device.
Figure 3:
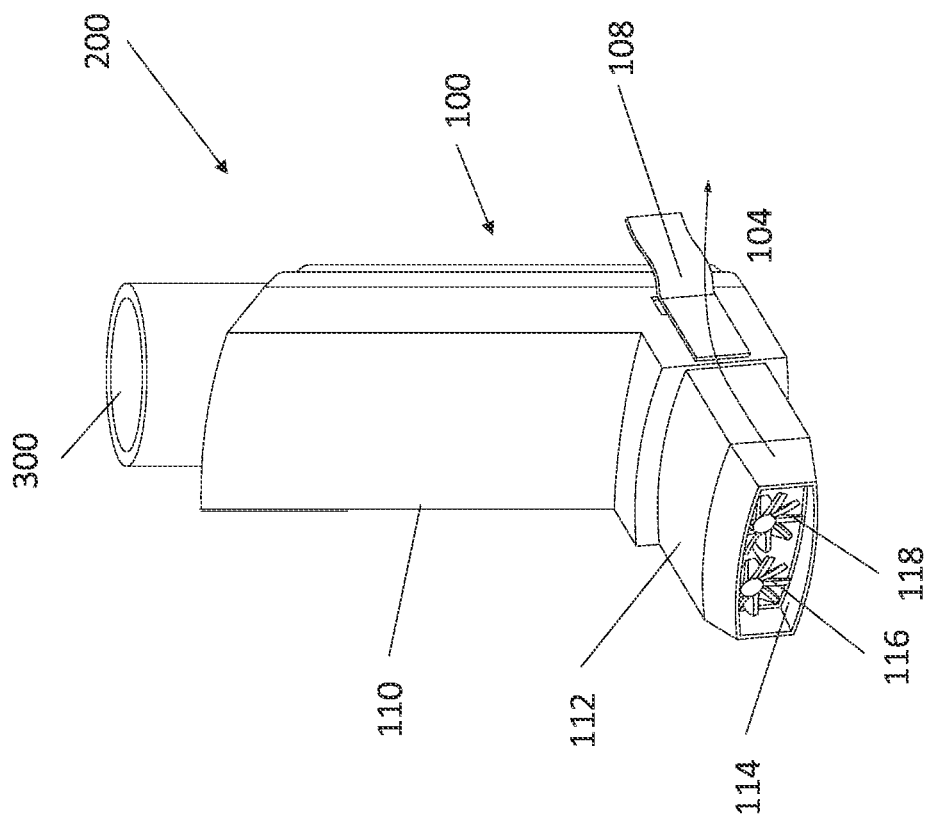

FIG. 1 illustrates an example use environment 400 that may make practical use of the health management systems, including a spirometer-inhaler device 100, described herein. For example, in the illustrated environment 400, one or more data collection devices 404 may collect data associated with a user 402. The data collection devices 404 may include the spirometer-inhaler device 100, as further described below with reference to FIGS. 2-4, one or more physiological sensors, one or more flow measurement devices, or other devices that may be used to monitor the health of the user. For example, the data collection devices 404 may include any device that may be used to monitor the respiratory health of the user. Example sensors may include optical heart rate sensors, electrical heart rate sensors accelerometers and gyroscopes, a GPS radio, temperature sensors, spectroscopic instruments, and/or other sensors. These example sensors may, for example, be used to take ECG readings, measure blood analytes, measure a user's movement, detect that a user is falling, or detect the user's position. Example devices may include measurement devices that measure one or more of: oxygen saturation, respiration rate, total hemoglobin levels, carboxyhemoglobin levels, methemoglobin levels, pulse-rate, pulse-rate variability, perfusion, Pleth variability index (PVI), pulmonary vascular resistance, and a variety of acoustic measurements. The spirometer-inhaler device 100 and the one or more data collection devices 404 may communicate with a backend system 410 through a network 408. Additionally or alternatively, the spirometer-inhaler device 100 and the one or more data collection devices 404 may communicate with one or more user devices 406. The user device 406 may include smart phones, tablet computers, laptop computers, smart watches, other mobile and wearable devices, desktop computers, networked televisions, networked game consoles, and/or the like. The device could also include a 3G/4G/5G modem for direct connection to the cloud to prevent the need for a smart phone. For example, the device 100 may measure a user's Forced Inspiratory Flow (FIF) value and display the user's FIF value on the user's smart phone or other electronic device. The one or more user devices 406 may communicate with the backend system 410 through a network 408.

The one or more user devices 406 can include a device associated with the user 402 of the one or more data collection devices 404, a device associated with a health care provider, a device associated with a third-party user, a device associated with a user's employer, the like or a combination thereof. For example, a user may measure the user's FIF value with the spirometer-inhaler device 100 and the spirometer-inhaler device 100 may transmit the user's estimated FIF value to the health care provider's device(s) so that the health care provider can monitor the user's respiratory health. Additionally, or alternatively, the device 100 can communicate the user's FIF value to the user's phone to display the user's FIF value on the phone's display and store the FIF value in the phone's memory so that the user can monitor the user's own respiratory health. For example, the user may download a mobile application associated with the spirometer-inhaler device 100 onto the user's phone or smartwatch. In order to access the user's respiratory health data, the user may access the mobile application and view the different physiological parameters being measured by the device 100 or the spirometer-inhaler system 200, as described below in reference to FIGS. 2-5. Moreover, in some embodiments, the device 100 can communicate the user's FIF value to the network 408. A user 402 and a health care provider may have respective login information to access the network 408 to monitor the user's 402 FIF values or other physiological parameters. In some examples, the one or more user devices 406 may upload, download, stream, display, analyze, read, write, access, or otherwise interact with data associated with the user 402, such as the data collected by the one or more data collection devices 404, data stored in the backend system 410 or other remote, non-local storage location, or data locally stored on the user devices 406. In some examples, the backend system 410 can include one or more hardware processors and/or storage systems capable of upload, download, display, analyze, read, write, access, or otherwise interact with the data or information associated with the user or other information associated with displaying and/or analyzing the data or information associated with the user.

The data collected by the spirometer-inhaler device 100, and the one or more data collection devices 404 can include a plurality of data associated with the user, including but not limited to health data. In some examples, health data can include heart rate, blood pressure, glucose, VO2 maximum, oxygen saturation, respiration rate, total hemoglobin levels, carboxyhemoglobin levels, methemoglobin levels, pulse-rate, pulmonary vascular resistance, symptoms and their severity, FIF, Force Expiratory Volume (FEV1), Forced Expiratory Flow (FEF), the like or a combination thereof. This collected data can be processed in a variety of different ways. For example, the spirometer-inhaler device 100 may include a processor that estimates a user's FIF value based on the user blowing into the device 100. The spirometer-inhaler device 100 may store the FIF data on a memory of the device 100 and display the FIF value on a display of the device 100. Additionally, or alternatively, the device 100 may send a measured value to a second device or the backend system 410, which processes the measured value to estimate a FIF value. The second device may display the estimated FIF value or the second device may send the FIF value to the device 100 so that the device 100 displays the FIF value.

FIGS. 2-5 illustrate different views of a spirometer-inhaler system 200 that can be used in the use environment 400 described in reference to FIG. 1. For example, the spirometer-inhaler system 200 may include a spirometer-inhaler device 100, a canister 300 configured to removably connect to the spirometer-inhaler device 100, one or more flow measurement devices (not shown) configured to removably connect to the spirometer-inhaler device 100, and/or one or more processors. The spirometer-inhaler system 200 may combine the assessment ability of a spirometer with the ability to deliver medication of an inhaler. Medication can include, for example, control medication or rescue medication associated with a respiratory disease, such as asthma.

Figure 4:
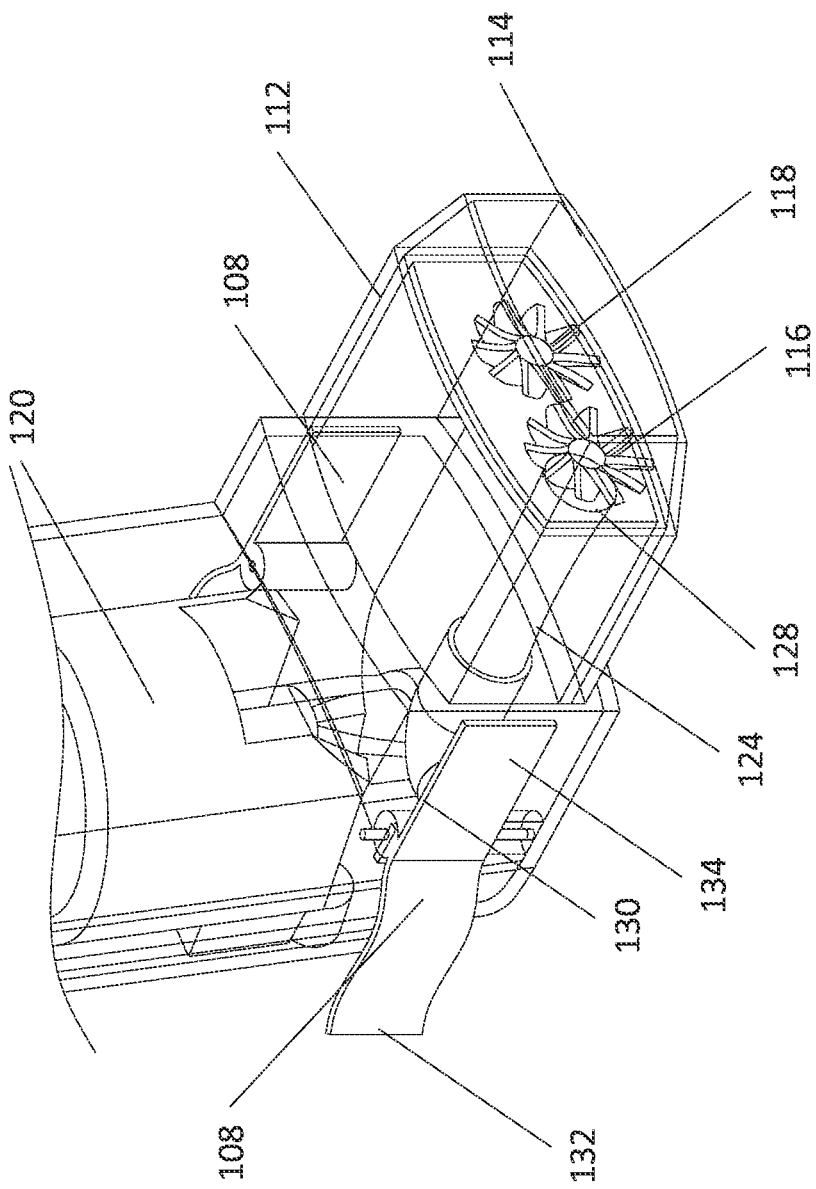
FIG. 4 illustrates a close up view of a component of a spirometer-inhaler device.
Figure 5:
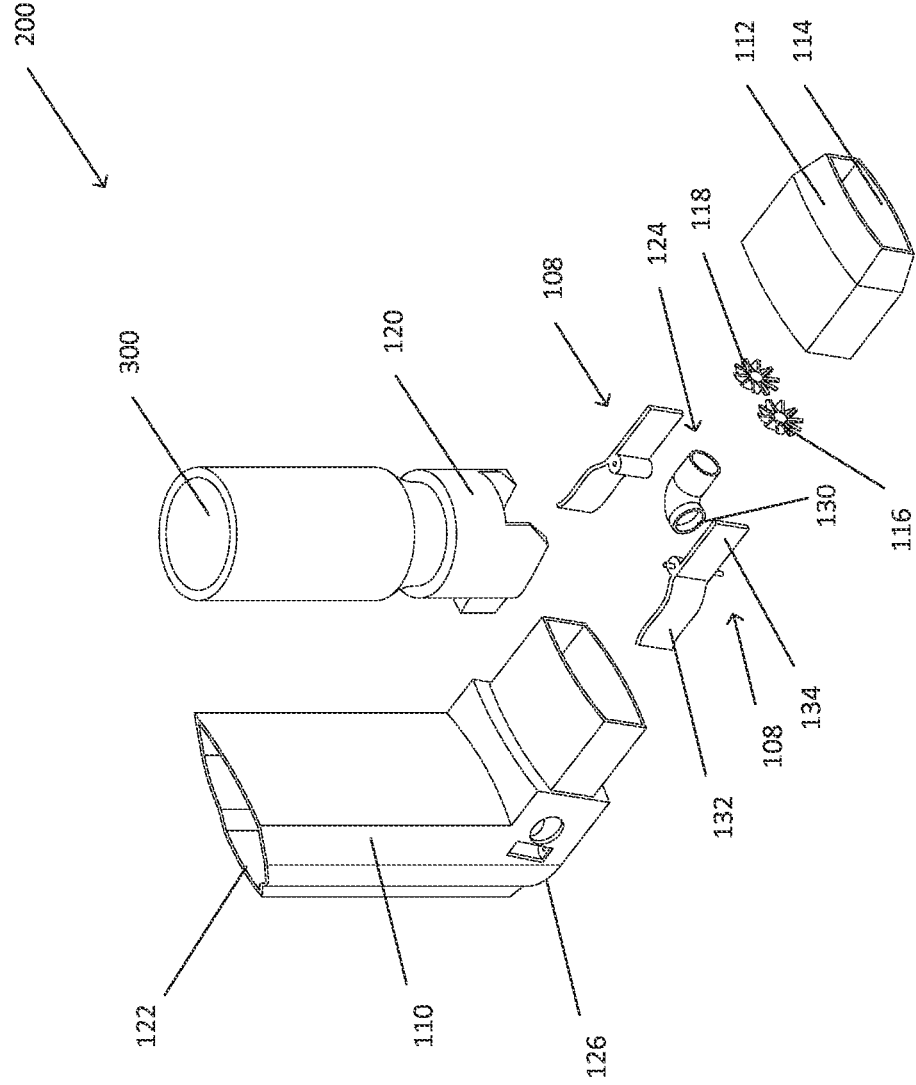
FIG. 5 illustrates an exploded view the spirometer-inhaler device shown in FIGS. 2-3.

In some aspects, the spirometer-inhaler device 100 may include a first portion 110 and a second portion 112. In some embodiments, the device 100 may include a general L-shape, similar to a standard inhaler, with the first portion 110 forming the vertical component and the second portion 112 forming the horizontal component. Although the device 100 is shown as including a general L-shape, other shapes are contemplated. For example, the device may be cylindrical, conical, spherical, or have another shape in whole or in part. The first portion 110 may include a one-way valve 120, a first end 122 including a top opening, and a central cavity. The central cavity of the first portion 110 can extend from the first end 122 through the center of the first portion 110 and be configured to removably receive the canister 300. In some aspects, the first portion 110 itself can be one of the two (or more) channels required for flow estimations. The first portion 110 can have a one-way valve 120 (such as illustrated in FIGS. 4 and 5) to improve the simplicity of the device 100. In some aspects, the one-way valve 120 may be configured to removably connect with the canister 300. For example, the one-way valve 120 may include a threaded recess configured to engage with a threading on an end of the canister 300 such that the end of the canister 300 can be sealed to the one-way valve 120 while a body portion of the canister 300 can be housed within the central cavity of the first portion 110. Additionally or alternatively, the canister 300 may removably connect to the one-way valve 120 with a snap-fit engagement, detent, or other coupling mechanism. The canister 300 may form a seal with the one-way valve 120 so as to prevent a user's expiratory flow from traveling via a first flow path 106 of the system 200, as described below. The one-way valve 120 may be configured to allow fluid to flow from the canister 300 to an opening 114 of the second portion 112 and prevent fluid from flowing in the opposite direction. In some examples, the second portion 112 can include at least a portion of the first flow path 106. In addition to, or alternative to, the one-way valve 120, the first portion 110 can include an internal gap or aperture within the central cavity of the first portion 110 adapted to allow fluid to flow from the canister 300 to the opening 114 of the second portion 112 and prevent fluid from flowing in the opposite direction.

In some aspects, the second portion 112 of the device 100 may extend from the first portion 110, adjacent a second end 126 of the first portion 110 opposite the first end 122. The second portion 112 may include a mouth piece 112 with an opening 114 and at least one propeller 116, 118. In some embodiments, the system 200 may include a turbine with a turning wheel. In some embodiments, the system 200 includes the canister 300. The canister 300 may be a medicine canister that holds control medication, rescue medication, or the like.

In some configurations, the disclosed system 200 can include two or more flow paths 104, 106. A first flow path 106 of the two or more flow paths may include the canister 300, the one-way valve 120 of the first portion 110, and/or the second portion 112. The direction of the first flow path 106 is indicated by arrow 106 in FIG. 2. The one-way valve 120 can be configured to direct medication from the canister 300 along the first flow path 106 to the user during inhalation while preventing the user's exhaled breaths from traveling along the first flow path 106. The second portion 112 may optionally include a first propeller 118 positioned in the first flow path 106 adjacent to the opening 114 of the second portion 112. The first propeller 118 may be configured to better deliver the medication into the user's lungs. For example, when a user places the mouthpiece 112 in the user's mouth and inhales to administer the medication, a negative flow rate is created that may cause the first propeller 118 to spin and propel the medication from the canister 300 into the user's mouth. Additionally or alternatively, the first propeller 118 spinning can notify the one or more processors of the system 200 that the medication is being administered and the one or more processors of the system 200 can detect how much of the medication was administered and the depth of the user's breath. For example, the one or more processors of the system 200 may be configured to measure the amount of medication administered and the depth of the user's inhaled breath when the first propeller 118 begins spinning. The measured depth of the user's inhaled breath can be used as another variable to estimate various physiological parameters of the user.

In some configurations, the spirometer-inhaler system 200 can take additional measurements to enable better predictive capacity of FEV1 or FEF. For example, the system 200 can utilize the patient's inhalation to better estimate common respiratory measurements. Moreover, the system 200 can use additional measurements, such as oxygen saturation, respiration rate, and the like, to improve the estimation of all variable types listed in the present disclosure. For example, these additional measurements can be utilized as spot-check, trended, or modeled forms of these data types.

In some configurations, the system 200 includes a second flow path 104 that may include portions of the second portion 120. The direction of the second flow path 104 is indicated by arrow 104 in FIGS. 2 and 3. The second portion 120 may further include an interior flow pathway 124 and a second propeller 116. The system 200 is configured to direct the user's exhaled breaths along the second flow path 104. For example, referring to FIGS. 4 and 5, a user may exhale into the opening 114 and the user's exhaled breath is directed through the interior flow pathway 124. For example, the interior flow pathway 124 can comprise one or more tubes or one or more ribs adapted to guide the second flow path 104. A first end 128 of the interior flow pathway 124 can be positioned adjacent the opening 114 and the second propeller 116. A second end 130 of the interior flow pathway 124 can be positioned on a side portion of the first portion 110, adjacent the second end 126 of the first portion 110. Although the first and second ends 128, 130 of the interior flow pathway 124 are illustrated in this manner, the first and second ends 128, 130 may be located anywhere on the device 100 that allows for at least two flow paths 104, 106.

In some aspects, the second end 130 of the interior flow pathway 124 is configured to be removably connected to the one or more flow measurement devices. The one or more flow measurement devices can include devices that measure FT values, FEV1 values or FEF values. When the one or more flow measurement devices are connected to the interior flow pathway 124, the second flow path 104 may include the one of the one or more flow measurement devices.

The interior flow pathway 124 may include a hole, which extends from the first end 128 of the interior flow pathway 124 to the second end 130 of the interior flow pathway 124, that may be smaller than the wider standard holes of current spirometers. For example, the hole of the interior flow pathway 124 can be approximately half to a quarter of the size of the wider standard holes of current spirometers.

As described above, the system 200 can comprise one or more processors. The processor(s) may be located within the spirometer-inhaler device 100, the one or more flow measurement devices, and/or the backend system 410. In some embodiments, the processor(s) can be configured to extrapolate the measurements from the smaller hole of the interior flow pathway 124 to assess the air flow of the wider standard holes of current spirometers. The smaller hole enables the prediction of FIF, FEV1 or FEF without requiring the user to completely expel the air (or completely deplete the air) from their lungs. Advantageously, reducing the amount of lung depletion may improve user comfort. In some configurations, the processor may also be configured to upload, download, display, analyze, read, write, access, or otherwise interact with the data or information associated with the user, such as data collected by the one or more data collection device 404 including the device 100 and/or the one or more flow measurement devices, or other information associated with displaying and/or analyzing the data or information associated with the user.

Additionally or alternatively, the one or more processors of the system 200 may estimate biometric parameters other than FIF, FEV1, or FEF, including, but not limited to, Force Vital Capacity (FVC), Maximal Voluntary Ventilation (MVV), Inspiratory Reserve Volume (IRV), Expiratory Reserve Volume (ERV), Residual Volume (RV), Functional Residual Capacity (FRC), Total Lung Capacity (TLC), IC (Inspiratory Capacity), tidal volume, vital capacity, and Maximal Inspiratory Pressure (MIP), and Maximal Expiratory Pressure (MEP). To effectively estimate some of these other values, the user may have to deplete their lungs.

In some aspects, the second flow path 104 may include a turbine with a first end and a second end. The first end of the turbine can include a turning wheel that can be adapted to cause the airflow that passes through the turning wheel to rotate helically. The turbine can also include a vane between the turning wheel and the second end of the turbine. The helically rotating airflow can cause the internal vane to rotate. The rotations of the internal vane can be detected by a sensor which can send the sensor signals to the one or more processors. The processor(s) can determine certain physiological parameters related to a patient's lung functionality. For example, the processor(s) can determine a user's FIF, FEV1 and/or FEF values.

In some embodiments, the system 200 may comprise a memory configured to store user's instructions. For example, one or more processors of the system 200 may access the user's instructions from the memory and display the instructions on a display of the system 200. The user's instructions may instruct the user on how to measure different physiological parameters with the system 200. For example, if the user wants to measure the user's FVC value, the user's instructions may include instructing the user to deplete the user's lungs into the device 100. Additionally or alternatively, the user can access the user's instructions on the user's phone via the mobile application associated with the spirometer-inhaler device 100. In some aspects, the user can access the user's instructions on any of the user devices 406 via an application, a website, or the like.

In some configurations, the spirometer-inhaler system 200 may further include a display (not shown) configured to display relevant information, one or more sensors, a battery, and a transmitter. In some aspects, the display can be positioned on the spirometer-inhaler device 100 and be electronically connected to the battery and the one or more processors. Additionally or alternatively, the display may be positioned on the one or more user devices 406 and/or the one or more flow measurement devices. For example, when a user blows into the device 100, the display can show the estimated FIF value. In some embodiments, the device 100 may include one or more sensors that can be electronically connected to the one or more processors and the battery. Additionally or alternatively, the one or more sensors may be located within the one or more flow measurement devices. The one or more sensors may include one or more differential pressure sensors.

In some configurations, the transmitter that can be electronically connected to the battery and the one or more processors. Additionally or alternatively, the transmitter may be located within the one or more flow measurement devices. In some aspects, the transmitter may be configured to transmit the health data from the device 100 or the one or more flow measurement devices to the network 408, the back end system 410, and/or the one or more user devices 406.

In some embodiments, one or more covers 108 may be incorporated in the second flow path 104 to enable switching between the one or more flow measurement devices. For example, the one or more covers 108 can include one or more shutters 108 with a lever portion 132 connected to a cover portion 134 configured to cover the second end 130 of the interior flow pathway 124. The user can push on the lever portion 132 removing the cover portion 134 from the second end 130 of the interior flow pathway 124, thereby opening the second flow path 104. With the second flow path 104 open, the user can removably connect an external device to the second flow path 104. The external device, for example, can include the one or more flow measurement devices. Additionally, or alternatively, the one or more covers 108 may include a manual plug, a cover adapted to open and close via a rotation mechanism, a mechanical iris, a cuspid one-way valve, a flap, or the like.

Terminology

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the implementation, certain acts, events, or functions of any of the processes or algorithms described herein can be performed in a different sequence, can be added, merged, or left out altogether (for example, not all described operations or events are necessary for the practice of the algorithm). Moreover, in certain implementations, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the disclosure herein can be implemented as electronic hardware (for example, ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the disclosure herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. A processor device can include an FPGA or other programmable device that performs logic operations without processing computer-executable instructions. A processor device can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the disclosure herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A system for delivering a medication to a user and measuring one or more physiological parameters of the user, the system comprising:
   a spirometer-inhaler device comprising:
      a first portion configured to removably receive a medicine canister;
      a second portion extending from the first portion, the second portion comprising a mouthpiece, wherein the mouthpiece comprises an opening and a plurality of propellors;
      a first flow path configured to direct a medication from the medicine canister to the opening of the mouthpiece, wherein the first flow path comprises a first propellor of the plurality of propellors adjacent the opening; and
      a second flow path configured to direct exhaled air from the opening of the mouthpiece to one or more flow rate measurement devices, wherein the second flow path comprises a second propellor of the plurality of propellors adjacent the opening;
   the medication canister configured to deliver the medication to the first portion of the spirometer-inhaler device; and
   one or more measurement devices configured to estimate one or more physiological parameters of the user, the one or more measurement devices comprising the one or more flow rate measurement devices.

2. The system of claim 1, wherein the spirometer-inhaler device further comprises a central hole configured to removably receive the medicine canister.

3. The system of claim 2, wherein the spirometer-inhaler device further comprises a one way valve configured to removably connect to the medicine canister and to direct the medication from the medicine canister to the opening of the mouthpiece.

4. The system of claim 3, wherein the medicine canister is configured to deliver the medication to the one way valve.

5. The system of claim 3, wherein the first flow path comprises the one way valve and the opening of the mouthpiece.

6. The system of claim 2, wherein the central hole comprises an internal gap configured to direct the medication from the medicine canister to the opening of the mouthpiece.

7. The system of claim 1, wherein the spirometer-inhaler device further comprises an interior flow pathway with a first end and a second end.

8. The system of claim 7, wherein the first end of the interior flow pathway is located adjacent the opening of the mouthpiece, wherein the second end of the interior flow pathway is located on a side portion of the first portion.

9. The system of claim 8, wherein the second flow path comprises the interior flow pathway and the opening of the mouthpiece.

10. The system of claim 9, wherein the second end of the interior flow pathway is configured to be connectable to the one or more flow rate measurement devices.

11. The system of claim 7, wherein the interior flow pathway includes one or more of: one or more interior tubes or one or more interior ribs.

12. The system of claim 1, wherein the one or more flow rate measurement devices are configured to estimate at least one of: forced inspiratory flow, forced expiratory volume, forced expiratory flow, forced vital capacity, maximal voluntary ventilation, inspiratory reserve volume, expiratory reserve volume, residual volume, functional residual capacity, total lung capacity, inspiratory capacity, tidal volume, vital capacity, maximal inspiratory pressure, or maximal expiratory pressure.

13. The system of claim 1, wherein the one or more flow rate measurement devices are configured to be connectable to the second flow path.

14. The system of claim 1, wherein the one or more measurement devices are configured to measure at least one of: oxygen saturation, respiratory rate, total hemoglobin level, level of carboxyhemoglobin, level of methemoglobin, pulse rate, or acoustic measurements.

15. The system of claim 1, further comprising a display.

16. The system of claim 15, wherein the display is disposed on one or more of: the spirometer-inhaler device, the one or more measurement devices, or one or more user devices.

17. The system of claim 1, further comprising a transmitter.

18. The spirometer-inhaler device of claim 17 wherein the transmitter is configured to transmit the one or more physiological parameters of the user to one or more of: a network, a backend system, or one or more user devices.

* * * * *

UNITED STATES PATENT AND TRADEMARK OFFICE
CERTIFICATE OF CORRECTION

| | | |
|---|---|---|
| PATENT NO. | : 12,029,844 B2 | Page 1 of 1 |
| APPLICATION NO. | : 17/355752 | |
| DATED | : July 9, 2024 | |
| INVENTOR(S) | : Kevin Hughes Pauley et al. | |

It is certified that error appears in the above-identified patent and that said Letters Patent is hereby corrected as shown below:

On the Title Page

Page 4, Column 1 item (56) (U.S. Patent Documents), Line 63, delete "Ai-Ali" and insert -- Al-Ali --.

In the Specification

Column 7, Line 59, delete "FT" and insert -- FIF --.

Column 13, Line 16, delete "spirometer-inhaler device" and insert -- system --.

Signed and Sealed this
Eighteenth Day of March, 2025

Coke Morgan Stewart
*Acting Director of the United States Patent and Trademark Office*